United States Patent [19]
Holland et al.

[11] Patent Number: 5,686,247
[45] Date of Patent: Nov. 11, 1997

[54] DETECTION OF MAMMARY TUMOR VIRUS ENV GENE-LIKE SEQUENCES IN HUMAN BREAST CANCER

[75] Inventors: James Holland, Scarsdale; Beatriz Pogo, Pelham, both of N.Y.

[73] Assignee: Mount Sinai School of Medicine of the City University of New York, New York, N.Y.

[21] Appl. No.: 555,394

[22] Filed: Nov. 9, 1995

[51] Int. Cl.$^6$ .............................. C12Q 1/68; C12Q 1/70; C12Q 19/34; C07H 21/04
[52] U.S. Cl. .................... 435/6; 435/5; 435/91.2; 536/23.1; 536/24.3; 536/24.33
[58] Field of Search .......................... 435/6, 5, 91.2; 536/23.1, 24.3, 24.33

[56] References Cited

PUBLICATIONS

Wang et al., Cancer Res. 55:5173–5179, 1995.
Holland et al., Proc. Amer. Assoc. Cancer Res. 35:218 1300, 1994.
Wooster et al., Science 265:2088–2090, 1994.
DiFronzo et al., J. Virol. 67:3763–3770, 1993.
Miki et al., Science 266:66–71, 1994.
Barnabas–Sohi et al., Breast Die. 6:13–26, 1993.
Faff et al., J. Gen. Virol. 76:1087–1097, 1992.
Schuuring et al., Cancer Res. 52:5229–5234, 1992.
Morris et al., Oncogene Res. 6:53–63, 1991.
Runnebaum et al., Proc. Natl. Acad. Sci. USA 88:10657–10661, 1991.
Wright et al., PCR Protocols, Innis et al., eds., Academic Press, 1990, pp. 153–158.
Hareuveni et al., Int. J. Cancer 46:1134–1135, 1990.
Roelink et al., Proc. Natl. Acad. Sci. USA 87:4519–4523, 1990.
May et al., Cancer Res. 49:3879–3883, 1989.
Litvinov, et al., Acta Virol. 33:137–142, 1989.
Zhou et al., Oncogene 2:279–282, 1988.
Liscia et al., Oncogene 4:1219–1224, 1989.
Lidereau et al., Oncogene Res. 2:285–291, 1988.

Slagle et al., Cellular and Molecular biology of Mammary Cancer, Kidwell et al., eds., Plenum Press, NY, 1987, pp. 275–306.
Moore et al., J. Virol. 61:480–490, 1987.
Dickson et al., Nature 326:833, 1987.
Ono et al., J. Virol. 60:589–598, 1986.
Delli Bovi et al., Cancer Res. 46:6333–6338, 1986.
Deen et al., J. Virol. 57:422–432, 1986.
Casey et al., Mol. Cell Biol. 6:502–509, 1986.
Crepin et al., Biochem. Biophys. Res. Comm. 118:324–331, 1984.
Keydar et al., Proc. Natl. Acad. Sci. USA 81:4188–4192, 1984.
Westley et al., Gene 28:221–227, 1984.
Peters et al., Cell 33:369–377, 1983.
Redmond et al., J. EMBO 2:125–131, 1983.
Majors et al., J. Virol. 47:495–504, 1983.
Lloyd et al., Cancer 51:654–661, 1983.
Callahan et al., Proc. Natl. Acad. Sci. USA 79:5503–5507, 1982.
Nusse et al., Cell 31:99–109, 1982.
Witkin et al., J. Clin. Invest. 67:216–222, 1981.
Day et al., Proc. Natl. Acad., Sci. USA 78:2483–2487, 1981.
Zotter et al., Eur. J. Cancer 16:455–467, 1980.
Cesarone et al., Anal. Biochem. 100:188–197, 1979.
Mesa–Tejada et al., Proc. Natl. Acad. Sci. USA 75:1529–1533, 1978.
Yang et al., J. Natl. Cancer Inst. 61:1205–1207, 1978.
Axel et al., Nature 235:32–36, 1972.
Levine et al., Proc. Am. Assoc. Cancer Res. 21:170, 1980.

*Primary Examiner*—W. Gary Jones
*Assistant Examiner*—Dianne Rees
*Attorney, Agent, or Firm*—Brumbaugh, Graves, Donohue & Raymond

[57] ABSTRACT

The present invention relates to materials and methods for diagnosing breast cancer in humans. It is based, at least in part, on the discovery that a substantial percentage of human breast cancer tissue samples contained nucleic acid sequences corresponding to a portion of the mouse mammary tumor env gene. In contrast, such sequences were absent in almost all other human tissues tested.

14 Claims, 10 Drawing Sheets

```
MMTENV   974 TCCTCACTGCCAGATCGCCTTTAAGAAGGACGCCTTCTGGGAGGGAGACG 1023
             |||||||||| ||||||||||||||||||||||||||||||||||||||:
MS1627     1 TCCTCACTGNCAGATCGCCTTTAAGAAGGACGCCTTCTGGGAGGGAGACG   50

MMTENV  1024 AGTCTGCTCCTCCACGGTGGTTGCCTTGCCCTTGACCAAGGGGTG       1073
             ||||||||||||||||||||||| ||||| ||||||||||||||||
MS1627    51 AGTCTGCTCCTCCACGGTGGTTGACTTGCGCCTTGACCAGGGGGTG       100

MMTENV  1074 AGTTTTCTCCAAAAGGGGGCCCTTGGGTTACTTTGGGATTTCTCCCTTCC 1123
             ||||||||||||||||||||||||||||||||||||||||||||||||||
MS1627   101 AGTTTTCTCCAAAAGGGGGCCCTTGGGTTACTTTGGGATTTCTCCCTTCC  150

MMTENV  1124 CTCGCCTAGTGTGTAGATCAGTCAGATCAGATTAAAAGCAAAAAGGATCTAT 1173
             |||||||||| |||||||||||||||||||||||||||||||||||||||
MS1627   151 CTCGCCTAGTGTAGATCAGTCAGATCAGATTAAAAGCAAAAAGGATCTAT  200

MMTENV  1174 TTGGAAATTATACTCCCCCAGTCAATAAAGAGGTTCATCGATGGTATGAA 1223
             ||||||||||||||||||||||||||||||||||||||||||||||||||
MS1627   201 TTGGAAATTATACTCCCCCTGTCAATAAAGAGGTTCATCGATGGTATGAA  250
```

FIG. 8A

```
MMTENV1224  GCAGGATGGGTAGAACCTACATGGTTCTGGGAAAATTCTCCTAAGGATCC  1273
            ||||||||||||||||||||||||||||||||||||||||||||||||||
MS1627  251 GCAGGATGGGTAGAACCTACATGGTTCTGGGAAAATTCTCCTAAGGATCC  300

MMTENV1274  CAATGATAGAGAGATTTTACTGCTCTAGTTCCCATACAGAATTGTTTCGCT  1323
            ||||||||||||||||||||||||||||||||||||||||||||||||||
MS1627  301 CAATGATAGAGAGATTTTACTGCTCTAGTTCCCATACAGAATTGTTTCGCT  350

MMTENV1324  TAGTTGCAGCCTCAAGATATCTTATTCTCAAAAGGCAGGATTTCAGGAA   1373
            |||||||||||||||||||||||||||| ||||||||||||||||||||
MS1627  351 TAGTTGCAGCCTCAAGATATCTTATTCCACAAAAGGCAGGATTTCAAGAA   400

MMTENV1374  CATGAGAGATG-ATCCCTACATCTCTGTGTTACTTACCCTTATGTCATATT  1423
            |||| || ||| |||| ||||||||||||||||||||||||| ||| | |
MS1627  401 CATGACACATGAATCCCTACATCTCTGTGTTACTTACCCTTATGCCANANT  450

MMTENV1424  ATTAGGATTACCTCAGCTAATAGAGATATAGAGAAAGAGAGGATCTACTTTTC  1473
            ||||||||||||||||||||||||||||||||| |||||||||||||||||
MS1627  451 ATTAGGATTACCTCAGCTAATAGAGATATAGAGGAAGAGAGGATCTACTTTTC  500
```

FIG. 8B

```
MMTENV1474  ATATTCCTGTTCTTCTTGTAGATTGACTAATTGTTTAGATTCTTCTGCC  1523
            ||||||||||||||||||||||||||||||||||||||||||||||||
MS1627  501 ATATTCCTGTTCTTCTTGTAGATTGACTAATTGTTTAGATTCTTCTGCC   550

MMTENV1524  TACGACTATGCAGCGATCATAGTCAAGAGGCCGCCATACGTGCTGCTACC  1573
            ||||||||||||||||||||||||||||||||||||||||||||||||||
MS1627  551 TACGACTATGCAGCGATCATAGTCAAGAGGCCGCCATACGTGCTGCTACC   600

MMTENV1574  TGTAGATATTGGTGATGAACCATGGTTTGATGATTCTGCCATTCAAAACCT  1623
            ||||||||||||||||||||||||||||||||||  ||||||| ||||||
MS1627  601 TGTAGATATTGGTGATGAACCATGGTTTGATGANNCTGCCANTCAAAACCT   650

MMTENV1624  TTAGGTATGCCACA GAT  1640
            |||||||| ||||| |||
MS1627  651 TTAGGTATNCCACA GAT   667
```

FIG. 8C

DETECTION OF MAMMARY TUMOR VIRUS ENV GENE-LIKE SEQUENCES IN HUMAN BREAST CANCER

INTRODUCTION

The present invention relates to materials and methods for diagnosing breast cancer in humans. It is based, at least in part, on the discovery that a substantial percentage of human breast cancer tissue samples contained nucleic acid sequences corresponding to a portion of the mouse mammary tumor env gene. In contrast, such sequences were absent in almost all other human tissues tested.

BACKGROUND OF THE INVENTION

A large body of information has accumulated about the molecular biology of MMTV (reviewed in Slagle, B. L. et al., 1987, in "Cellular and Molecular Biology of Mammary Cancer", Kidwell et al., eds., Plenum Press, NY. pp 275–306). Mouse mammary tumor virus (MMTV) is associated with a high incidence of breast cancer in certain strains of mice (over 90% among females), and has been regarded as a potential model for human disease.

The MMTV virus does not carry a transforming oncogene, but rather acts as an insertional mutagen with several proviral insertion loci designated int-1 or wnt-1 (Nusse R. et al., 1982, Cell 31:99–109) int-2 (Peters, G. et al., 1983, Cell 33:369–377) int-3 (Gallahan, D. et al., 1987, J. Virol. 61:218–220) int-4 (Roelink, H. et al., 1990, Proc. Natl. acad. Sci. U.S.A. 87:4519–4523) and int-5 (Morris, V. L., et al. 1991, Oncogene Research 6:53–63), which encode for growth factors or other related proteins. These genes are not expressed in normal mammary tissue but become activated after integration of MMTV provirus into the adjacent chromosomal DNA.

The human homolog of the int-2 locus has been located on chromosome 11 (Casey, G. et al., 1986, Mol. Cell Biol. 6:502–510) and has been found amplified (in 15% of the breast cancers) and also expressed (Lidereau, R. et al., 1988, Oncogene Res 2:285–291; Zhou, D. J. et al., 1988, Oncogene 2:279–282; Liscia, D. S. et al., 1989, Oncogene 4:1219–1224; Meyers, S. L. et al., 1990, Cancer Res 50:5911–5918). It may be significant that in tumors from Parsi women, who have a high incidence of breast tumors, the int-2 locus is amplified in 50% of the cases (Barnabas-Sohi, N. et al., 1993, Breast Dis. 6:13–26). The amplification of int-2 and other genes in 11q13 is indicative of poor prognosis (Schuwring, E. et al., 1992, Cancer Research 52:5229–5234; Champeme, M-H, et al., 1995, Genes, Chromosomes and Cancer 12:128–133). Both mouse and human int-2 have been sequenced (Moore, R. et al., 1986, EMBO J 5:919–924). The gene encodes a protein of about 27 kilodaltons (KD) which shows homology to both basic and acidic fibroblast growth factors (Dickson, C. et al. 1987, Nature (London) 326:833).

However, efforts to demonstrate the presence of viruses in human breast cancer through search for viral particles, immunological cross-reactivity, or sequence homology have yielded contradictory results. Detectable MMTV env gene-related antigenic reactivity has been found in tissue sections of breast cancer (Mesa-Tejada et al., 1978, Proc. Natl. Acad. Sci. U.S.A. 75:1529–1533; Levine, P. et al., 1980, Proc. Am. Assoc. Cancer Res. 21:170; Lloyd, R. et al., 1983, Cancer 51:654–661), breast cancer cells in culture (Litvinov, S. V. and Golovkina, T. V., 1989, Acta Virologica 33:137–142), human milk (Zotter S. et al., 1980, Eur. J. Cancer 16:455–467) in sera of patients (Day, N. K. et al., 1981, Proc. Natl. Acad. Sci. U.S.A. 78:2483–2487), in cyst fluid (Witkin, S. S. et al., 1981, J. Clin. Invest. 67:216–222) and in particles produced by a human breast carcinoma cell line (Keydar, I. et al., 1984, Proc. Natl. Acad. Sci. U.S.A. 81:4188–4192). Sequence homology to MMTV has been found in human DNA under low stringency conditions of hybridization (Callahan, R. et al., 1982, Proc. Natl. Acad. Sci. U.S.A. 79:5503–5507) and RNA related to MMTV has been detected in human breast cancer cells (Axel, R. et al., 1972, Nature 235:32–36). The presence of MMTV related sequences in lymphocytes from patients with breast cancer has been reported (Crepin, M. et al., 1984, Biochem. Biophys. Res. Comm. 118:324–331), as well as detection of reverse transcriptase (RT) activity in their monocytes (Al-Sumidaie, A. M. et al., 1988, Lancet 1:5–8). May and Westley (May and Westley, 1989, Cancer Research 49:3879–3883) have reported the presence of MMTV-like sequences arranged as tandem repeats only in DNA from breast cancer cells.

These results have been difficult to interpret, and theories linking MMTV or a related virus with human breast cancer have fallen out of favor, in view of the relatively recent discovery of human endogenous retroviral sequences ("HERs"; Westley, B. et al., 1986, J. Virol. 60:743–749; Ono, M. et al., 1986, J. Virol. 60:589–598; Faff, O. et al., 1992, J. Gen. Virology 73:1087–1097). Data which could be interpreted to demonstrate the presence of MMTV-related sequences could be more readily explained by endogenous human retroviral sequences. Adding further confusion to the picture, env-gene related antigenicity has been detected in epitopes of human proteins (Hareuveni, M. et al., 1990, Int. J. Cancer 46:1134–1135).

SUMMARY OF THE INVENTION

The present invention relates to methods for diagnosing breast cancer in humans in which the presence of mouse mammary tumor virus env gene-like sequences bears a positive correlation to the existence of malignant breast disease. It is based, at least in part, on the discovery that 38 to 40 percent of human breast cancer tissue samples tested contained gene sequences homologous to the mouse mammary tumor virus env gene that are substantially absent from other human tumors and tissues. The molecular probes used in these experiments were designed to avoid cross-hybridization with endogenous human retroviral sequences. The present invention further provides for compositions of molecular probes which may be utilized in such diagnostic methods.

DESCRIPTION OF THE FIGURES

FIG. 2: Nested PCR. A: 2% agarose gel electrophoresis. 1: Amplification of 686 bp of MMTV-like env gene sequences using primers 2 and 3 and the product of reaction A 1 as template. B, 1 and 2: Southern blot hybridization of the amplified products using probe $5'-^{32}P$ end-labeled probe 2a.

FIG. 8: Comparison of the nucleic acid sequence of mouse mammary tumor env gene ("MMTENV"), showing residues 976–1640 (SEQ. ID NO.17) with the nucleic acid sequence of a representative 660 bp sequence obtained by PCR reaction of DNA from human breast cancer tissue ("MS1627") (SEQ ID NO:18).

DETAILED DESCRIPTION OF THE INVENTION

Figure 1A:
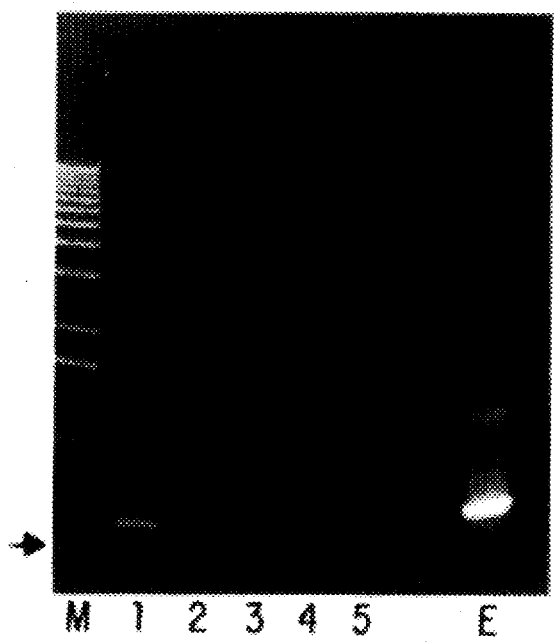
FIG. 1: Amplification of 660 bp of MMTV-like env gene. DNA was extracted from frozen tissues. PCR was performed using primers 1 and 3. A: 2% agarose gel electrophoresis. B: Southern blot hybridization using $5'^{32}P$-end-labeled probe 2. Lanes 1 and 3: breast cancer; lanes 2 and 4: normal breast; lane 5: control reaction (no DNA); lane E: MMTV env gene. M: molecular weight marker. Arrow indicates 510 bp band.

The present invention relates to methods and compositions for diagnosing breast cancer in humans.

The present invention provides for compositions comprising an isolated and purified nucleic acid molecule which (i) hybridizes to a gene of mouse mammary tumor virus; (ii) is present in at least 20 percent of DNA samples prepared from breast cancer tissue of different human subjects; and (iii) is present in less than 5 percent of DNA samples prepared from tissues other than breast cancer tissue from different human subjects. The term "hybridize" is used to refer to routine DNA-DNA or DNA-RNA hybridization techniques under what would be regarded, by the skilled artisan, as stringent hybridization conditions. The phrase "is present" indicates that a native form of the molecule, in an unpurified state (for example, as part of chromosomal DNA), may be detected by a standard laboratory technique, such as Southern blot or polymerase chain reaction (PCR). To be "present", the molecule may be detectable by one technique but not others. To be present in "less than 5 percent of DNA samples prepared from tissues other than breast cancer tissue from different human subjects", all non-breast cancer tissue samples are considered together, but the total number of samples must be large enough to give the 5 percent value statistical significance that would be reasonable to the skilled artisan.

In preferred embodiments of the invention, the mouse mammary tumor virus (hereafter "MMTV") gene is the env gene.

In order to identify such a nucleic acid molecule, the sequence of MMTV may be compared, using a computer database, to known human DNA sequences, and portions of MMTV which are less than or equal to 25 percent homologous to a human sequence may be selected for further study. The term "homologous", as used herein, refers to the presence of identical residues; for example, a first sequence is considered 25 percent homologous to a second sequence if it shares 25 percent of the residues of the first sequence. Since there is relatively greater likelihood that MMTV may bear similarity to human retroviral-like sequences, it may be preferable to evaluate whether a particular MMTV nucleic acid sequence is homologous to such sequences, for example, as endogenous human retrovirus sequences. A prototype of such viruses is HERV-K10 (Ono, M. et al., 1986, J. Virol. 60:589–598).

Once an MMTV gene sequence which is less than or equal to 25 percent homologous to a human DNA sequence, such as a human endogenous retroviral sequence, is identified, the presence of nucleic acid molecules having the MMTV gene sequence in human breast cancer tissues and other tissues may be evaluated. Such evaluations may be performed either by Southern blot techniques, or, preferably, by polymerase chain reaction (PCR) techniques, which are more sensitive. In such a way, MMTV gene sequences which (i) hybridize to at least 20 percent of DNA samples prepared from breast cancer tissue of different human subjects and (iii) hybridize to less than 5 percent of DNA samples prepared from human tissues other than breast cancer tissues may be identified. A nucleic acid molecule having a MMTV gene sequence which satisfies these requirements may then be used in diagnostic methods which detect the presence of such sequence in human breast tissue by standard techniques, including PCR techniques which assay for the presence of the molecule, but also, where appropriate, Southern blot, Northern blot, or Western blot techniques, to name but a few.

Figure 7:
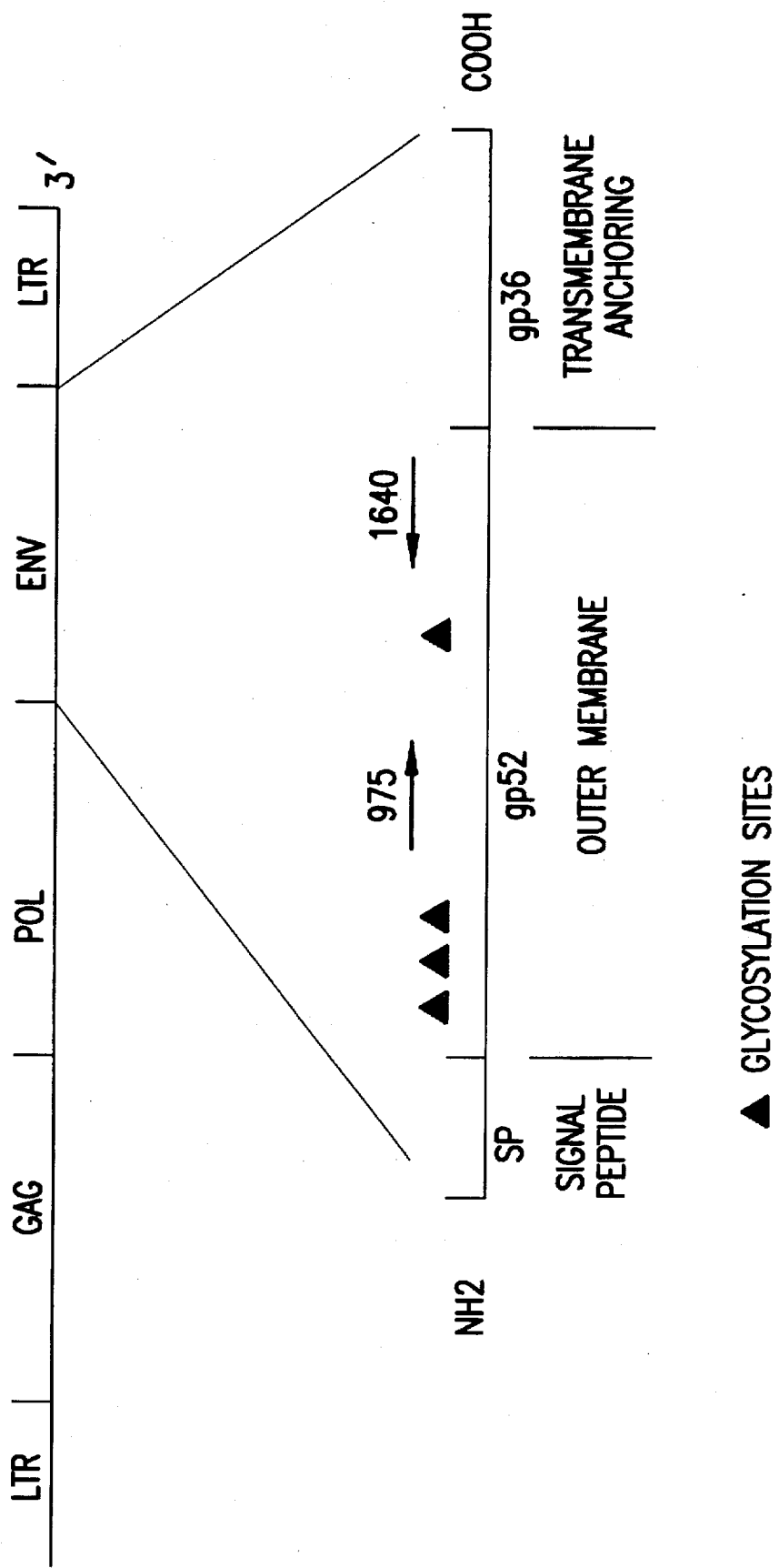
FIG. 7: Map of MMTV.

In preferred embodiments, the present invention relates to a portion of MMTV localized between MMTV env gene sequences 976 and 1640 (Majors, I. E. and Varmus, H. E., 1983, J. Virol. 47:495–504; see FIG. 7). This about 660 bp sequence (hereafter, "the 660 bp sequence") has been found to exhibit low (16 percent) homology to the prototype human endogenous retrovirus HERr-K10, using the IBI/ Pustell Sequence Analysis Program, and has also been shown to be present in 121 (38.5%) of 314 unselected breast cancer tissue samples, in cultured breast cancer cells, in 2 of 29 breast fibroadenomas (6.9%) and in 2 of 107 breast specimens from reduction mammoplasties (1.8%). The sequence was not found in normal tissues including breast, lymphocytes from breast cancer patients nor in other human cancers or cell lines (see example section, infra). Similarly, an about 250 bp sequence (hereafter "the 250 bp sequence"), between positions 1388 and 1640 in the env gene, and therefore falling within the 660 bp sequence, was detected in 60 (39.7%) of 151 breast cancer, and in one of 27 normal breast samples assayed from paraffin-embedded sections. Cloning and sequencing of the 660 bp and 250 bp sequences demonstrated that they are 95–99% homologous to MMTV env gene, but not to the known human endogenous retroviruses ("HERs") nor to other viral or human genes (<18%).

Nucleic acids having the 660 bp sequence or the 250 bp sequence may therefore be used, according to the invention, to diagnose breast cancer in a subject, using methods which include PCR and Southern blot methods. Where PCR methods are used, primers such as those listed in Table 1, below, may be utilized.

The present invention provides for compositions comprising essentially purified and isolated nucleic acid having the 660 bp sequence or the 250 bp sequence or an at least five bp, and preferably greater than or equal to ten bp, subsequence thereof. In order to maintain the desired specificity, such nucleic acid molecules may preferably contain sequence falling within the 660 bp sequence, but preferably do not contain sequences from other portions of the MMTV genome, which may, undesirably, hybridize to human sequences which are not breast cancer specific, such as HERs. Accordingly, the present invention provides for compositions wherein the isolated and purified nucleic acid molecule comprises at least a portion having a nucleic acid sequence which hybridizes to a region of the mouse mammary tumor virus env gene between residues 976 and 1640, or between residues 1388 and 1640, and wherein the isolated and purified nucleic acid molecule does not hybridize to any other region of the MMTV genome.

The 660 bp sequence, in various embodiments, may have a number of nucleotide sequences. For example, in one embodiment, the 660 bp sequence may have a sequence as set forth in FIG. 8 and designated "MMTENV" (SEQ ID NO.17), which depicts the MMTV env sequence between residues 976 and 1640. In a second series of embodiments, the 660 bp sequence may have a sequence as set forth in FIG. 8 and designated "MS1627", which depicts a predominant sequence for the 660 bp sequence as it has been defined by sequencing analysis of the products of PCR reactions using DNA from human breast cancer tissues. In still further embodiments, the 660 bp sequence may have various other nucleotide sequences obtained by sequencing the results of PCR reactions to detect the presence of 660 bp sequence in human breast cancer tissues.

In related embodiments, the present invention provides for compositions comprising PCR primers that may be used to detect the presence of the forementioned molecules. For example, the compositions may comprise one or more of the following primer molecules (5'-3'): CCTCACTGCCAGATC (SEQ ID. NO.1); GGGAATTCCTCACTGCCAGATC (SEQ ID. NO.2); CCTCACTGCCAGATCGCCT (SEQ ID. NO.3); TACATCTGCCTGTGTTAC (SEQ ID. NO.4); CCTACATCTGCCTGTGTTAC (SEQ ID. NO.5); CCGCCATACGTGCTG (SEQ ID. NO.6); ATCTGTGGCATACCT (SEQ ID. NO.7); GGGAATTCATCTGTGGCATACCT (SEQ ID. NO.8); ATCTGTGGCATACCTAAAGG (SEQ ID. NO.9); GAATCGCTTGGCTCG (SEQ ID. NO.10); CCAGATCGCCTTTAAGAAGG (SEQ ID. NO.11); TACAGGTAGCAGCACGTATG (SEQ ID. NO.12).

The use of such compositions and molecules in PCR and Southern blot techniques is illustrated in the non-limiting examples set forth below. The correlation between the presence of the MMTV-related nucleic acid molecules described above and breast cancer allows such molecules and compositions to be utilized in the diagnosis of breast cancer. Accordingly, the present invention provides for a method of diagnosing breast cancer, wherein the detection of such nucleic acid molecules bears a positive correlation to the existence of breast cancer in a human. The results of such evaluation, together with additional clinical symptoms, signs, and laboratory test values, may be used to formulate the complete diagnosis of the patient.

In further related embodiments, the present invention provides for an essentially purified peptide encoded by a nucleic acid molecule which (i) hybridizes to a gene of MMTV; (ii) is present in at least 20 percent of DNA samples prepared from breast cancer tissue of different human subjects; and (iii) is present in less than 5 percent of DNA samples prepared from tissues other than breast cancer tissue from different human subjects. In preferred embodiments, the MMTV gene is the env gene.

Such peptides may be used in the diagnosis of breast cancer. Accordingly, the present invention provides for a method of diagnosing breast cancer in a human subject, comprising detecting the presence of a peptide encoded by a nucleic acid molecule which (i) hybridizes to the env gene of a mouse mammary tumor virus; (ii) is present in at least 20 percent of DNA samples prepared from breast cancer tissue of different human subjects; and (iii) is present in less than 5 percent of DNA samples prepared from tissues other than breast cancer tissue from different human subjects.

The present invention also provides for antibodies (including monoclonal and polyclonal) antibodies which specifically bind to such peptides. Such antibodies may be used in methods of diagnosing breast cancer, for example, but not by way of limitation, by Western blot, dot blot, in situ hybridization, immunofluorescent techniques, and so forth.

In nonlimiting embodiments of the invention, the skilled artisan may evaluate MMTV-like nucleic acid molecules for regions which would be considered likely to encode immunogenic peptides (using, for example, hydropathy plots). Such peptides may then be sequenced and used to produce antibodies that may be employed in diagnostic methods as set forth above.

For example, certain peptides encoded by portions of the 660 bp sequence have been synthesized. These peptides, which have the sequences LKRPGFQEHEMI (SEQ ID. NO.13) and GLPHLIDIEKRG (SEQ ID. NO.14), have been used to produce antibodies in rabbits, and the resulting antisera have successfully identified breast cancer cells positive for MMTV env-like sequences by PCR assay. Other peptides encoded by 660 bp sequence which may be useful according to the invention include TNCLDSSAYDTA (SEQ ID. NO:15) and DIGDEPWFDD (SEQ ID. NO.16).

EXAMPLE: THE DETECTION OF MOUSE MAMMARY TUMOR VIRUS ENV GENE-LIKE SEQUENCES IN HUMAN BREAST CANCER CELLS AND TISSUES

Material and Methods

DNA from breast cancer tissue and other human cancer tissues, human placentas, normal human tissues including breast, and from several human cell lines (including eight breast cancer cell lines), and two normal breast cell lines was extracted following the procedure of Delli Bovi et al. (1986, Cancer Res. 46:6333–6338). The DNA was resuspended in a solution containing 0.05M Tris HCl buffer, pH 7.8, and 0.1 mM EDTA, and the amount of DNA recovered was determined by microfluorometry using Hoechst 33258 dye (Cesarone, C. et al., 1979, Anal Biochem 100:188–197). Plasmids containing the cloned genes of MMTV were obtained from the ATCC, propagated in *Eschericia coli* cultures and purified using anion-exchange minicolumns (Qiagen) or by precipitation with polyethylene glycol (Sambrook J., et al., 1989, in "Molecular Cloning/A Laboratory Manual", Cold Spring Harbor). Oligonucleotide primers were synthesized at the core facilities of the Brookdale Molecular Biology Center at Mount Sinai School of Medicine.

Polymerase chain reaction (PCR) was performed using Taq polymerase following the conditions recommended by the manufacturer (Perkin Elmer Cetus) with regard to buffer, $Mg^{2+}$ and nucleotide concentrations. Thermocycling was performed in a DNA cycler by denaturation at 94° C. for 3 min. followed by either 35 or 50 cycles of 94° C. for 1.5 min., 50° C. for 2 min. and 72° C. for 3 min. The ability of the PCR to amplify the selected regions of the MMTV env gene was tested by using as positive templates the cloned MMTV env gene and the genomic DNA of the MCF-7 cell line, since it was shown to express gp52 immunological determinants (Yang, N. S., et al., 1975, J. Natl. Cancer Inst. 61:1205–1208). Optimal $Mg^{2+}$, primer concentrations and requirements for the different cycling temperatures were determined with these templates. The master mix as recommended by the manufacturer was used. To detect possible contamination of the master mix components, a reaction without template was routinely tested. γ DNA and control primers provided by the manufacturer were used as control for polymerase activity. As an internal control, amplification of a 120 bp sequence estrogen receptor gene was assayed using primers designed and generously provided by Dr. Beth Schachter, (Mount Sinai School of Medicine, N.Y.). In addition, primers for actin 5 gene amplification were also used.

The product of the PCR was analyzed by electrophoresis in a 2% agarose gel. A 1 kb DNA ladder (Gibco BRL) was used to identify the size of the PCR product. To determine if the amplified sequences of the middle region of the 660 bp faithfully reproduced the sequences of the env gene of MMTV, an 18-mer sequence within the env gene was used as a probe for the 660 bp amplified sequence. The 18-mer probe was 5' end-labeled with $^{32}$P-ATP using T4 polynucleotide kinase and purified by the NENSORB nucleic acid purification cartridge (NEN). Southern blot hybridization was performed using the conditions described by (Saiki et al.,1985, Science 230:1350–1354).

The product of the PCR (660 bp or 250 bp) was cloned directly from the reaction mixture into the TA cloning vector (Invitrogen) using the TA cloning kit and following the conditions recommended by the supplier. Direct cloning of the fragment isolated from the gel, was also performed. Plasmid DNA was purified by CsCl density gradient centrifugation or by precipitation with polyethylene glycol (Sambrook et al., 1989, in "Molecular Cloning/A Laboratory Manual", Cold Spring Harbor), restricted with HindIII and EcoRI, electrophoresed in 2% agarose gels and transferred to nitrocellulose filters. Southern blot hybridization was carried out using a 5'-terminal labeled internal probe as described above. Cloning procedures were performed in laboratories totally separate from those where PCR was carried out. Automated DNA sequencing (using Applied Technology Sequencer Model 373A) was performed in the Brookdale Molecular Biology Center. Sequence homology was determined using the IBI MacVector GenBank and GCG Programs.

To prevent contamination of the samples, processing of human tissues was performed in a laminar flow hood. DNA extractions were done in a chemical hood located in a different room from that were PCR was performed. PCR assays were assembled in a biological hood provided with ultraviolet light. Aerosol resistant tips and dedicated positive-displacement pipettes were used throughout. All equipment used for PCR (microcentrifuge, electrophoresis apparatus, pipettors) was cleaned each time with 10% sodium hypochlorite to assure DNA decontamination (Prince and Andrus, 1992, Biotechniques 12:358–36). After the initial experiments were performed, the plasmid containing the MMTV env gene was frozen and never used again, to avoid contamination. However, to detect plasmid contamination from our own env gene clones, primers were designed to amplify plasmid sequences. All the MMTV env positive samples were then tested for plasmid contamination.

Southern blotting and hybridization were performed as described (Southern, E. M., 1975, J. Mol. Biol. 98:503–517), using the 660 bp cloned sequences labeled by the random primer procedure (Feinberg, A. P., et al., 1983, Anal. Biochem. 132:6–13). Prehybridization and hybridization were performed in a solution containing 6×SSPE, 5% Denhardt's, 0.5% SDS, 50% formamide, 100 μg/ml denaturated salmon testis DNA, incubated for 18 hrs at 42° C., followed by washings with 2×SSC and 0.5% SDS at room temperature and at 37° C. and finally in 0.1×SSC with 0.5% SDS at 68° C. for 30 min (Sambrook et al., 1989, in "Molecular Cloning/A Laboratory Manual", Cold Spring Harbor). For paraffin-embedded tissue sections the conditions described by Wright and Manos (1990, in "PCR Protocols", Innis et al., eds., Academic Press, pp. 153–158) were followed using primers designed to detect a 250 bp sequence.

RESULTS

Selection of Specific MMTV env Gene Sequences

A computer search for MMTV env gene homologous sequences was first performed, since sequence homology between the human endogenous retroviral sequences and MMTV had been described. The prototype of this group of human endogenous retroviruses is HERV-K10 (Ono, M. et al., 1986, J. Virol. 60:589–598). The sequences of the env gene of MMTV (Majors, I. E. and Varmus, H. E., 1983, J Virol 47:495–504) were aligned with sequences of the env gene of the human endogenous retrovirus HERV-K10 (Ono, M. et al., 1986, J. Virol. 60:589–598), using the IBI/Pustell Sequence Analysis Program. A region of 660 bp of low homology (16%) was localized between MMTV env gene sequences 976 and 1640 (Majors, I. E. and Varmus, H. E., 1983, J Virol 47:495–504). This internal domain of the outer membrane of the env gene has only one glycosylation site and is highly conserved between strains. Two primers comprising 15 bp sequences at positions 976–990 (primer 1) and 1626–1640 (primer 3) were first synthesized. Later longer primers were synthesized (1N and 3N). An 18-mer sequence in the middle of the 660 bp MMTV env region (1388–1405) (primer 2) was used as a probe to identify the 660 bp sequence. A second oligomer probe was synthesized comprising the sequence 1554 to 1568 (primer 2a) to be used for hybridization when a sequence of around 250 bp (between positions 1388 and 1640) was amplified. For nested PCR reactions (Mullis, K. B. and Faloona, F. A., 1987, Meth Enzymol 155:335–350), another primer comprising sequences 1647 to 1661 (primer 4) was synthesized to be used with primer 1 in the first reaction and primers 2 and 3 in the second. Modified primers with GC clamps and extra sequences were also synthesized and used in the PCR (primers 1a and 3a). Another set of primers comprising sequences 974 to 1003 (5L) and 1558 to 1577 (3L) were subsequently developed because their Tm's matched and provided better amplification than the original primers. The sequences are represented in Table 1. All of them were productive in amplification reactions.

TABLE 1

Primer and probe sequences and location in mouse mammary tumor virus envgene

| Designation | Sequence (5'-3') | Location |
|---|---|---|
| 1 (SEQ. ID. NO:1) | CCTCACTGCCAGATC | 976-990 |
| 1a | GGGAATTCCTCACTGCCAGATC | 976-990 |

TABLE 1-continued

Primer and probe sequences and location in mouse mammary tumor virus envgene

| Designation | Sequence (5'-3') | Location |
|---|---|---|
| (SEQ. ID. NO:2) 1N | CCTCACTGCCAGATCGCCT | 976-993 |
| (SEQ. ID. NO:3) 2 | TACATCTGCCTGTGTTAC | 1388-1405 |
| (SEQ. ID. NO:4) 2N | CCTACATCTGCCTGTGTTAC | 1386-1405 |
| (SEQ. ID. NO:5) 2a | CCGCCATACGTGCTG | 1554-1568 |
| (SEQ. ID. NO:6) 3 | ATCTGTGGCATACCT | 1640-1626 |
| (SEQ. ID. NO:7) 3a | GGGAATTCATCTGTGGCATACCT | 1640-1626 |
| (SEQ. ID. NO:8) 3N | ATCTGTGGCATACCTAAAGG | 1640-1621 |
| (SEQ. ID. NO:9) 4 | GAATCGCTTGGCTCG | 1661-1647 |
| (SEQ. ID. NO:10) 5L | CCAGATCGCCTTTAAGAAGG | 984-1003 |
| (SEQ. ID. NO:11) 3L | TACAGGTAGCAGCACGTATG | 1558-1577 |
| (SEQ. ID. NO:12) | | |

Detection of MMTV-Like env Gene Sequences in Human Breast Tumor DNA

Figure 1B:

PCR was performed on DNA extracted from breast cancer tissues, normal breast tissues and from the plasmid containing the env gene of MMTV, using primers 1 and 3. Photographs of the ethidium bromide stained gels of the PCR product reveal the presence of an approximately 660 bp sequence in some of the tumors, (FIG. 1A, lanes 1 and 3) but not in the normal tissue samples (FIG. 1A, lanes 2 and 4). As a positive control the MMTV env gene was also amplified (FIG. 1A, lane E). Similar results were obtained with modified primers 1a, 3a, 3L and 5L. Southern blot hybridization of the gel with $^{32}$P-labeled 18-mer oligonucleotide indicated that this internal sequence was present in the amplified material (FIG. 1B) and that the bands in the gel were not artifactual.

Our initial effort was to analyze a representative sample of breast cancer specimens as well as normal tissues and other tumors. To date 343 breast tumors have been processed, DNA extracted and PCR preformed. Of these 343 tumors, 314 were carcinomas and 29 were fibroadenomas. Amplification of sequences of 660 bp was observed in 121 of the carcinomas (38.5%) and in 2 of the 29 fibroadenomas (6.9%). These sequences were confirmed to be MMTV env gene-like sequences by hybridization with the labeled specific probe containing the internal sequences. These sequences were not detected in the DNAs extracted from 20 normal organs, 23 cancers from other organs and 26 samples of blood lymphocytes including 7 from breast cancer patients whose breast specimens were positive. From 107 samples of normal breast obtained from reduction mammoplasties, 2 were positive (1.8%). In addition to DNA from lymphocytes from seven positive patients, DNA from their normal homolateral breast tissue was tested in 4 cases. All were negative (Table 2). Finally, DNA of the MCF-7, and ED (a cell line developed in our laboratory from the pleural effusion of a patient with an env -positive breast tumor) breast cancer cell lines were shown to contain the 660 bp MMTV env gene-like sequences (Table 3), while four other breast cancer cell lines were positive only for the 250 bp sequence (T47-D, BT-474, BT-20 and MDA-MB-231).

TABLE 2

Detection of MMTV envgene-like sequences in human DNA extracted from fresh or frozen tissues

| Sample | Number | MMTV envgene sequences | % Positive |
|---|---|---|---|
| Breast Carcinomas | 314 | 121 | 38.5% |
| Breast Fibroadenomas | 29 | 2 | 6.9% |
| Normal Breasts | 107 | 2 | 1.8% |
| *Normal Breasts | 4 | negative | |
| Tumors other than breast | 23 | negative | |
| Normal tissues | 20 | negative | |
| Lymphocytes | 26 | negative | |
| **Lymphocytes | 7 | negative | |

*Histologically normal tissue from same breast as positive cancer.
**Lymphocytes from breast cancer patients who were positive for MMTV envgene sequences in the tumor.

TABLE 3

Detection of MMTV envgene-like sequences in DNA from human cell lines in culture

| Human Cell Lines | MMTV envgene sequence |
|---|---|
| MC-7 (breast carcinoma) | positive |
| T47-D (breast carcinoma) | negative |
| BT-20 (breast carcinoma) | negative |
| MDA-MB-231 (breast carcinoma) | negative |
| ZR-75-1 (breast carcinoma) | negative |
| SK-BR 3 (breast carcinoma) | negative |
| BT474 (breast carcinoma) | negative |
| ED (breast carcinoma) | positive |
| MCF-10 (normal breast) | negative |
| HB-447 (normal breast) | negative |
| HL-60 (promyelocytic leukemia) | negative |
| K562 (erythroleukemia) | negative |
| Jurkat (T cell leukemia) | negative |
| Hep 6-2 (hepatoma) | negative |

Figure 2A:
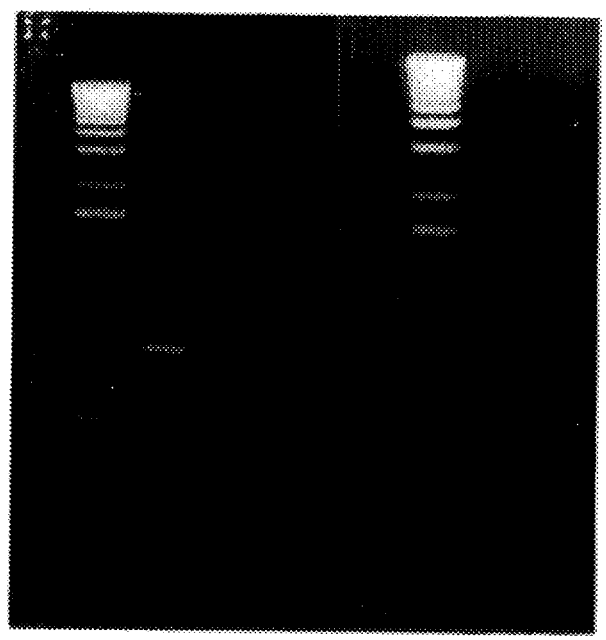
Figure 2B:
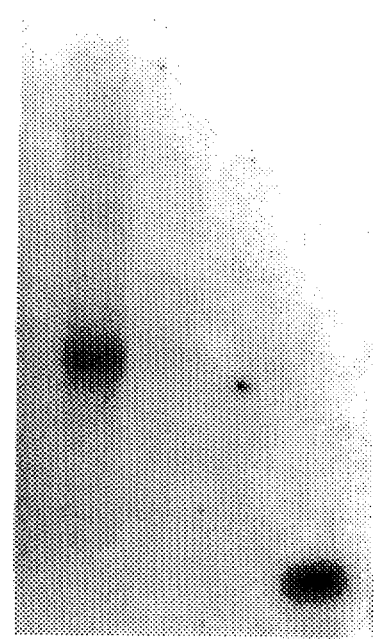

The nested polymerase reaction was used in several instances to increase sensitivity and specificity, thus reducing the probability of false positives. In FIG. 2, results of a representative nested reaction are shown using primers 1 and 4 in the first reaction (FIG. 2A) and 2 and 3 for the 2nd reaction. The specificity of the reaction can be seen in the 2nd amplification (FIG. 2B).

Figure 3A:
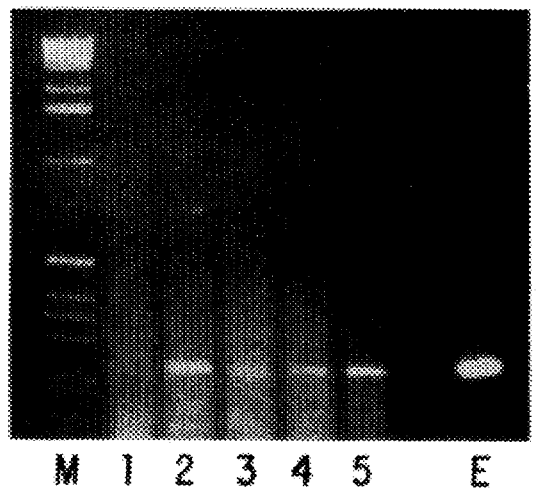
FIG. 3: Amplification of 250 bp of MMTV-like env gene. DNA was extracted from paraffin-embedded tissue sections. PCR was performed using primers 2 and 3. A: 2% agarose gel electrophoresis. B: Southern blot hybridization using 5'-$^{32}$P-labeled probe 2a. Lane 1: normal breast; lanes 2 to 5: breast cancer; lane E: MMTV env gene. M: molecular weight marker. Arrow indicates 298 bp band.
Figure 3B:
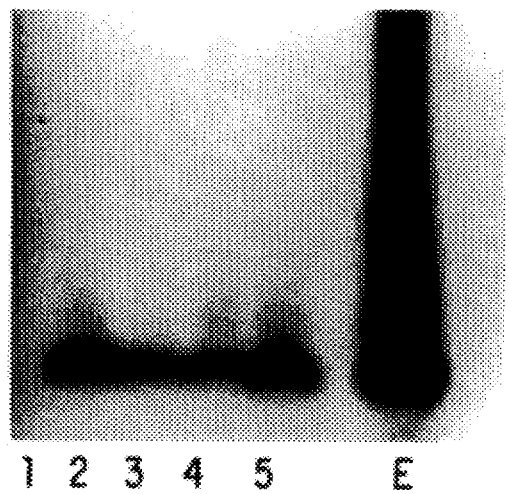

To study a large number of samples and to be able to perform archival studies, PCR of paraffin-embedded tissue sections was also carried out. Primers 2 and 3 were used to amplify a 250 bp sequence within the 660 bp stretch when DNA was extracted from paraffin-embedded tissue sections since larger size sequences are difficult to amplify after fixation. Tumor DNA was amplified (FIG. 3A, lanes 2-5) whereas normal breast DNA was not (FIG. 3A, lane 1). The identification of this 250 bp sequence with the MMTV-like env gene was confirmed by hybridization with an internal probe (primer 2a) as shown in FIG. 3B. Using this procedure we have analyzed 151 breast cancer samples and found that 60 (39.7%) possess the 250 bp sequence. Of the 27 normal breast samples obtained from reduction mammoplasties assayed by this procedure, one was positive (3.7%). These results, in conjunction with those obtained from lymphocytes and normal breast tissue of patients whose breast cancer was PCR positive, indicate that MMTV-like sequences are present in a significant number of human breast cancer DNA which cannot be explained by DNA polymorphism.

Cloning and Sequencing of the MMTV-Like env Gene Sequence

Figure 4:
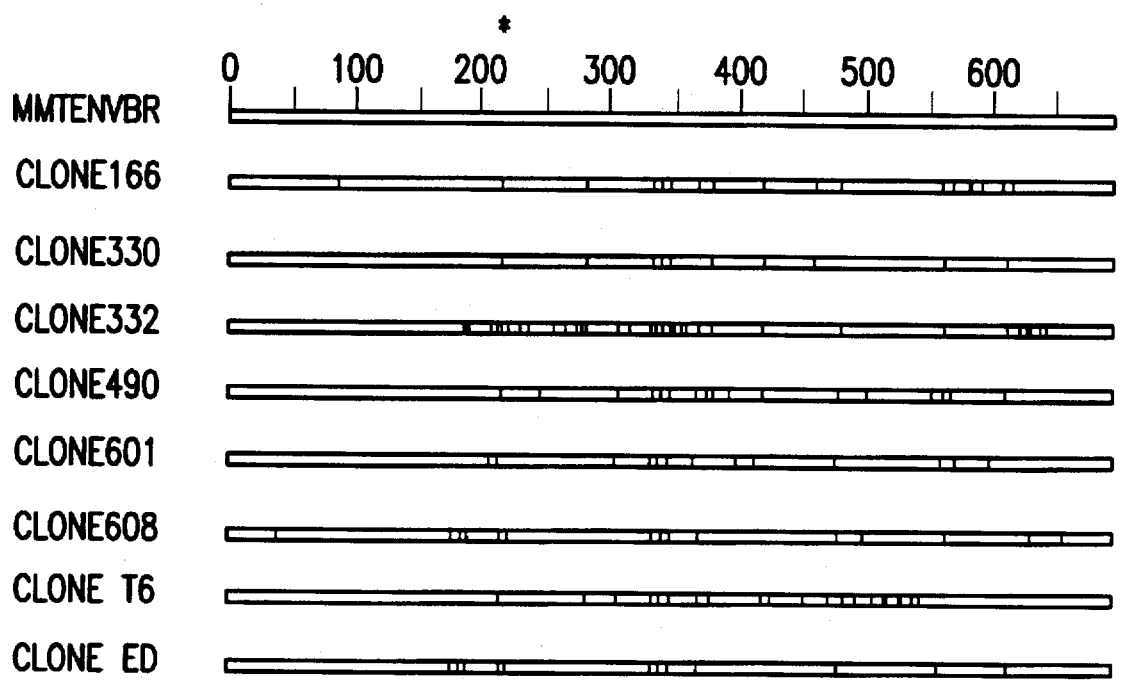
FIG. 4: Nucleotide sequence of the cloned MMTV env gene-like sequences as compared to the env sequences of the GR and BR6 strains of MMTV using the GCG program. *:potential glycosylation site, l:mismatch to MMTV.
Figure 4:
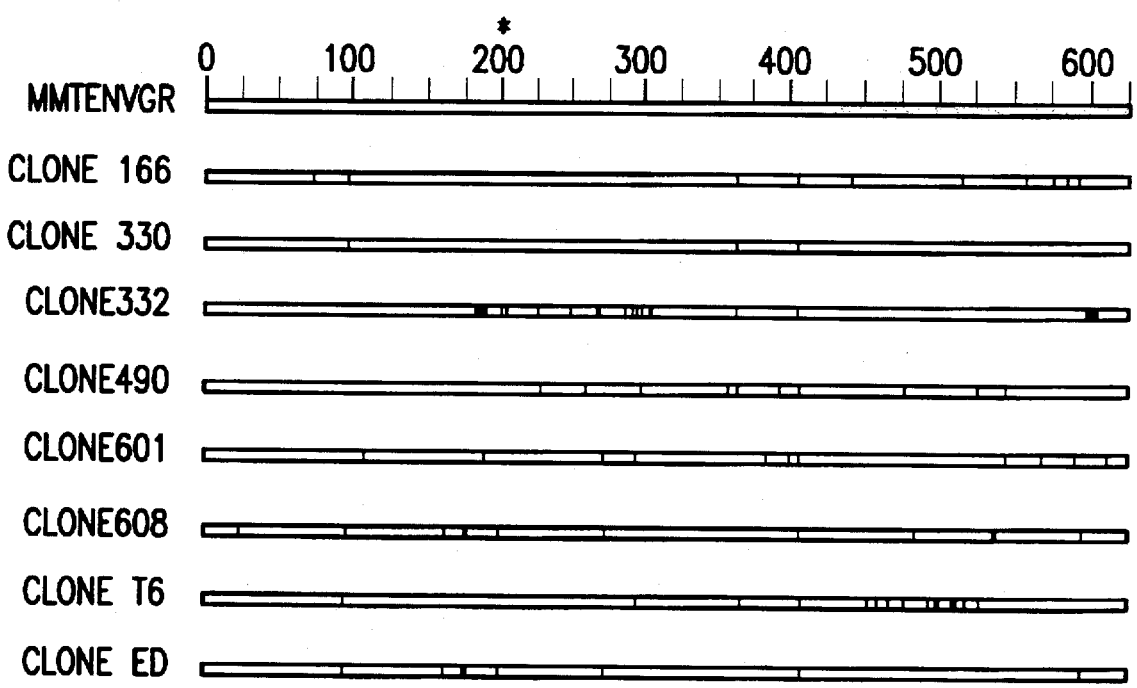

To find out whether there was homology to MMTV env gene throughout the whole 660 bp stretch, the product of the PCR from 8 different tumors was cloned and sequenced. In FIG. 4 the sequence of different clones comprising around 600 bp are represented, as aligned to the MMTV env gene sequence of the GR and BR6 strains (Redanon, S. and Dickson, C., 1983, EMBO J. 2:125–131). This domain of the env gene in the GR strain is 100% homologous to the $C_3H$ strain and 98% to the BR6 strain (Majors, I. E. and Varmus, H. E., 1983, J. Virol. 47:495–504;Moore, R. et al., 1987, J. Virol. 61:480–490). Evaluation of the clones indicated that homology to MMTV env gene varied from 95% to 99%. Another seven clones comprising only 250 bp were also sequenced. Homology to MMTV env gene varied from 95% to 99% (data not shown). When compared to the human endogenous provirus HERV-K10, the homology of all the clones was less than 15%. When compared against all known viral and human genes using the IBI MacVector GenBank and GCG programs, the highest homology recorded was 18%.

Southern Blot Analysis Using Cloned Sequences

Figure 5:
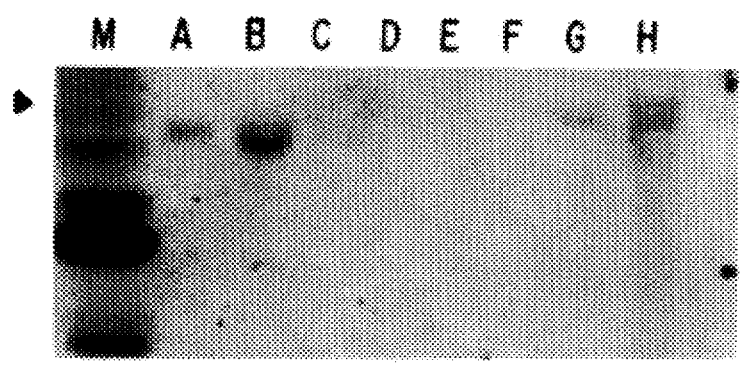
FIG. 5: Southern blot hybridization of genomic DNA. DNA was extracted from frozen tissues or cell lines, digested with EcoR1 and transferred to nitrocellulose paper. Hybridization with $^{32}$P-labeled clone 166. DNA from A, B, and G:env gene positive breast cancer; C and D: env negative breast cancer; E and F: normal breast; H:MCF-7 cells. M: molecular weight marker, Arrow indicates 9 kb band.
Figure 6:
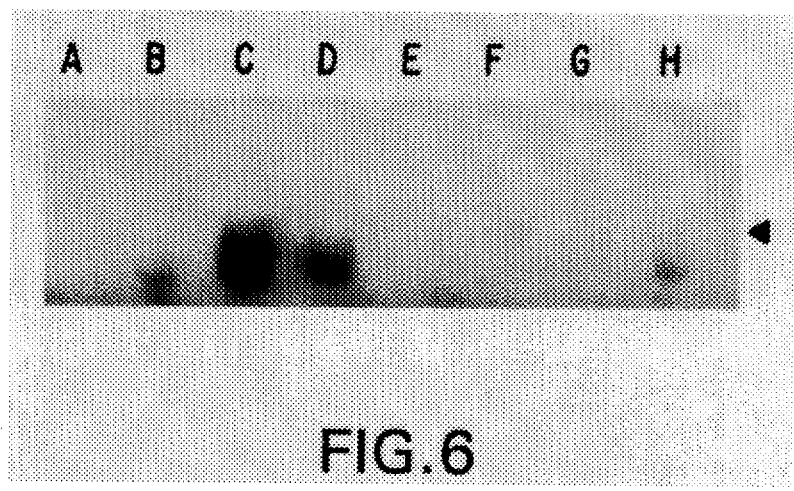
FIG. 6: Southern blot hybridization of genomic DNA. Experimental conditions as in FIG. 5. DNA from A and B: env negative breast cancer; C and D: env positive breast cancer; E: molecular weight marker (non-labelled); f. to h: normal breast. Arrow indicates position of 9 kb marker.

To investigate whether the env gene-like sequences were present in human DNA, Southern blot hybridization was performed using the cloned sequence as probe. DNAs from normal breast tissues, env positive or negative breast tumors, tumors other than breast and breast cancer cell lines were restricted with EcoRI and in some instances with PstI, BglII or KpnI. EcoRI is a frequent cutter restriction enzyme that digests MMTV proviral DNA between env and pol genes. Four different cloned 660 bp sequences were used as probes after labeling with $^{32}P$ by random prime-labeling. Results of some of the Southern blot hybridization experiments are shown in FIG. 5. They reveal the presence of a labeled restriction fragment migrating at approximately 7–8 kb in breast cancer DNA, in ED and two fragments in MCF-7 cells. Different restriction patterns were observed with the other three enzymes. The 660 bp sequence was absent in 10 normal tissues, 10 fibroadenomas and 10 tumors from other tissues. It is important to emphasize that hybridization conditions for these experiments were stringent to avoid interference with endogenous sequences that might interact with the probes.

Discussion

Search for virus-related sequences in human breast cancer has been hampered by great variation reported in previous studies, by the presence of endogenous retroviral sequences in human DNA and by the lack of sensitivity of the methods employed. The studies reported herein circumvent these deficiencies by focusing on sequences with low homology to human endogenous retroviruses, by investigating a large number of tumors and several types of controls and by using the most sensitive technology presently available.

The results indicate that unique MMTV env gene sequences were present in 38.5% of the breast cancer samples analyzed and 39.7% of archival samples of breast cancer and that these sequences were absent in normal tissues including lymphocytes from patients with positive breast cancer and in cancers other than breast. Normal breast tissue and fibroadenomas had a low frequency (1.8 to 6.9%) of positive results. When cloned and sequenced, the sequences were found to be highly homologous to MMTV env gene, but not to the endogenous retroviral sequences. Furthermore, experiments in which the cloned amplified sequences were used for hybridization with DNA from breast cancer or normal tissues revealed that homologous DNA was only present in breast cancer DNA.

The detection of MMTV env gene sequences in two fibroadenomas out of 29 and in two normal breast tissue samples out of 107 samples is of uncertain significance. Although such results could potentially be artifactual, and thus may represent false positives, they may alternatively indicate the presence of histologically unrecognized cells that were or will be neoplastic.

Ninety percent (90%) of the breast cancers tested were invasive ductal carcinomas, which reflects the prevalence of this type of neoplasm. Most patients were node-positive which is probably artifactual since it was necessary that tumor size be sufficiently large to provide an aliquot for research and tumor size correlates with node positivity.

It is unlikely that differences in homology between MMTV env gene and the cloned human sequences are generated by errors committed by the Taq polymerase. It has been estimated that the rate of nucleotide misincorporation is $1\times10^{-5}$ per cycle (Ehrlich et al, 1991, Science 252:1643–1651) and therefore, only a total of 0.32 nucleotides misincorporated should be expected in 660 bp after 50 cycles. The differences in homology between clones from different patients is likely to represent heterogenicity of the env gene.

In contrast to earlier, ambiguous data associating MMTV-like sequences with human breast cancer, we have clearly demonstrated the existence of such sequences in breast cancer cells which cannot be explained by any known human endogenous retroviral sequence. Our data does not support the results of earlier studies which indicated that, as in the mouse, MMTV-like sequences were found in lymphocytes from two patients with breast cancer (Crepin, M. et al., 1984, Biochem. Biophys. Res. Comm. 118:324–331). The absence of MMTV env-like sequences in lymphocytes could reflect the fate a unique lymphocyte subset over decades between initial encounter and the appearance of clinical breast cancer; alternatively, the human disease may differ from the mouse model. Attempts to identify unique MMTV-like pol gene sequences cannot be distinguished from endogenous reverse transcriptase sequences (Deen, K. C. and Sweet, R. W., 1986, J. Virol. 57:422–432).

The origin of the MMTV env gene-like sequences found in tumor DNA could be the result of integrated MMTV-like sequences from a human mammary tumor virus. Polymorphism of endogenous retroviral sequences is conceivable but can be ruled out because these sequences were not detected in lymphocytes from the positive patients, in sections of breast with tumors in which abnormal cells were absent nor in normal breast tissue. Recombination during tumorigenesis between endogenous sequences to resemble the MMTV env genes seems highly unlikely since no known or viral sequence is more than 18% homologous to the 660 bp sequence. Thus, the most conservative interpretation is that our findings represent exogenous sequences from an agent similar to MMTV. Recombination between endogenous and exogenous env gene sequences are known to accelerate the development of malignancies in mice (DiFronzo, N. L. and Holland, C. A., 1993, J. Virol. 67:3763–3770). Whether the 660 bp sequences belong to an entire acquired provirus or to an exogenous fragment integrated into the endogenous sequences, is presently not known. Experiments are in progress to distinguish between these possibilities.

Several genetic alterations have been identified in human breast cancer that can be useful as markers for prevention, detection or prognosis (reviewed in Runnenbaum, I. et al., 1991, Proc. Natl. Acad. Sci. U.S.A. 88:10657–10661). BR Ca-1 and 2 genes have recently been described. They account for at least 5% of the BC and are related to familial BC (Miki, Y. et al., 1994, Science 266:66–71; Wooster, R. et al., 1994, Science 265:2088–2090). We have primary evidence that familial clustering of the MMTV env gene-like sequences occurs, accounting for an even higher percentage of cancers in affected families (Holland et al. 1994, Proc. Am. Assoc. Cancer Res 35:218). The presence of MMTV env gene like sequences may be correlated with special clinical disease status, may provide another potential molecular marker, and may distinguish a subset of human breast cancer for which viral etiology is tenable. This has implications for epidemiology, therapy and prevention.

Various publications are cited herein, the contents of which are hereby incorporated by reference in their entireties.

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:

( x i ) SEQUENCE DESCRIPTION: SEQ ID NO:1:

CCTCACTGCC AGATC     15

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:

( x i ) SEQUENCE DESCRIPTION: SEQ ID NO:2:

GGGAATTCCT CACTGCCAGA TC     22

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA (i i i) HYPOTHETICAL: NO (i v) ANTI-SENSE: NO (v) FRAGMENT TYPE:

(v i) ORIGINAL SOURCE:

(i x) FEATURE:

(x i) SEQUENCE DESCRIPTION: SEQ ID NO:3:

CCTCACTGCC AGATCGCCT 19

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(i x) FEATURE:

(x i) SEQUENCE DESCRIPTION: SEQ ID NO:4:

TACATCTGCC TGTGTTAC 18

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(i x) FEATURE:

(x i) SEQUENCE DESCRIPTION: SEQ ID NO:5:

CCTACATCTG CCTGTGTTAC 20

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(vi) ORIGINAL SOURCE:

(ix) FEATURE:

(xi) SEQUENCE DESCRIPTION: SEQ ID NO:6:

CCGCCATACG TGCTG 15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:7:

ATCTGTGGCA TACCT 15

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:

(xi) SEQUENCE DESCRIPTION: SEQ ID NO:8:

GGGAATTCAT CTGTGGCATA CCT 23

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:

( x i ) SEQUENCE DESCRIPTION: SEQ ID NO:9:

ATCTGTGGCA TACCTAAAGG                                                                          20

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:

( x i ) SEQUENCE DESCRIPTION: SEQ ID NO:10:

GAATCGCTTG GCTCG                                                                                15

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:

( x i ) SEQUENCE DESCRIPTION: SEQ ID NO:11:

CCAGATCGCC TTTAAGAAGG                                                                          20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:

( x i ) SEQUENCE DESCRIPTION: SEQ ID NO:12:

TACAGGTAGC AGCACGTATG                                                                          20

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:13:

```
Leu Lys Arg Pro Gly Phe Gln Glu His Glu Met Ile
 1               5                  10
```

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:14:

```
Gly Leu Pro His Leu Ile Asp Ile Glu Lys Arg Gly
 1               5                  10
```

( 2 ) INFORMATION FOR SEQ ID NO:15:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:15:

```
Thr Asn Cys Leu Asp Ser Ser Ala Tyr Asp Thr Ala
 1               5                  10
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:16:

Asp Ile Gly Asp Glu Pro Trp Phe Asp Asp
1               5                   1 0

( 2 ) INFORMATION FOR SEQ ID NO:17:

( i ) SEQUENCE CHARACTERISTICS:
        ( A ) LENGTH: 662 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:17:

| | | | | | |
|---|---|---|---|---|---|
| TCCTCACTGC | CAGATCGCCT | TTAAGAAGGA | CGCCTTCTGG | GAGGGAGACG | AGTCTGCTCC | 60 |
| TCCACGGTGG | TTGCCTTGCG | CCTTCCCTGA | CCAAGGGGTG | AGTTTTCTC | CAAAAGGGGC | 120 |
| CCTTGGGTTA | CTTTGGGATT | TCTCCCTTCC | CTCGCCTAGT | GTAGATCAGT | CAGATCAGAT | 180 |
| TAAAAGCAAA | AAGGATCTAT | TTGGAAATTA | TACTCCCCCA | GTCAATAAAG | AGGTTCATCG | 240 |
| ATGGTATGAA | GCAGGATGGG | TAGAACCTAC | ATGGTTCTGG | AAAATTCTC | CTAAGGATCC | 300 |
| CAATGATAGA | GATTTTACTG | CTCTAGTTCC | CATACAGAAT | TGTTTCGCTT | AGTTGCAGCC | 360 |
| TCAAGATATC | TTATTCTCAA | AAGGCAGGAT | TTCAGGAACA | TGAGATGATT | CCTACATCTC | 420 |
| TGTGTTACTT | ACCCTTATGT | CATATTATTA | GGATTACCTC | AGCTAATAGA | TATAGAGAAA | 480 |
| GAGGATCTAC | TTTTCATATT | TCCTGTTCTT | CTTGTAGATT | GACTAATTGT | TTAGATTCTT | 540 |
| CTGCCTACGA | CTATGCAGCG | ATCATAGTCA | AGAGGCCGCC | ATACGTGCTG | CTACCTGTAG | 600 |
| ATATTGGTGA | TGAACCATGG | TTTGATGATT | CTGCCATTCA | AACCTTTAGG | TATGCCACAG | 660 |
| AT | | | | | | 662 |

( 2 ) INFORMATION FOR SEQ ID NO:18:

( i ) SEQUENCE CHARACTERISTICS:
        ( A ) LENGTH: 663 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:18:

-continued

| | | | | | | |
|---|---|---|---|---|---|---|
| TCCTCACTGN | CAGATCGCCT | TTAAGAAGGA | CGCCTTCTGG | GAGGGAGACG | AGTCTGCTCC | 60 |
| TCCACGGTGG | TTGACTTGCG | CCTTCCCTGA | CCAGGGGGTG | AGTTTTTCTC | CAAAAGGGGC | 120 |
| CCTTGGGTTA | CTTTGGGATT | TCTCCCTTCC | CTCGCCTAGT | GTAGATCAGT | CAGATCAGAT | 180 |
| TAAAAGCAAA | AAGGATCTAT | TTGGAAATTA | TACTCCCCCT | GTCAATAAAG | AGGTTCATCG | 240 |
| ATGGTATGAA | GCAGGATGGG | TAGAACCTAC | ATGGTTCTGG | GAAAATTCTC | CTAAGGATCC | 300 |
| CAATGATAGA | GATTTTACTG | CTCTAGTTCC | CATACAGAAT | TGTTTCGCTT | AGTTGCAGCC | 360 |
| TCAAGATATC | TTATTCACAA | AAGGCAGGAT | TTCAAGAACA | TGACATGAAT | CCCTACATCT | 420 |
| CTGTGTTACT | TACCCTTATG | CCANANTATT | AGGATTACCT | CAGCTAATAG | ATATAGAGGA | 480 |
| AGAGGATCTA | CTTTTCATAT | TTCCTGTTCT | TCTTGTAGAT | TGACTAATTG | TTTAGATTCT | 540 |
| TCTGCCTACG | ACTATGCAGC | GATCATAGTC | AAGAGGCCGC | CATACGTGCT | GCTACCTGTA | 600 |
| GATATTGGTG | ATGAACCATG | GTTGATGAN | NCTGCCANTC | AAACCTTTAG | GTATNCCACA | 660 |
| GAT | | | | | | 663 |

What is claimed is:

1. A composition comprising an oligonucleotide primer which may be used to detect the presence of a nucleic acid molecule which (i) hybridizes to the env gene of a mouse mammary tumor virus; (ii) is present in at least 38 percent of DNA samples prepared from breast cancer tissue of different human subjects; and (iii) hybridizes to less than 7 percent of DNA samples prepared from tissues other than breast cancer tissue from different human subjects wherein said oligonucleotide primer is capable of specifically hybridizing with said nucleic acid molecule.

2. The composition of claim 1, wherein the oligonucleotide primer comprises the sequence CCTCACTGCCAGATC (SEQ ID. NO.1).

3. The composition of claim 1, wherein the oligonucleotide primer comprises the sequence GGGAATTCCTCACTGCCAGATC (SEQ ID. NO.2).

4. The composition of claim 1, wherein the oligonucleotide primer comprises the sequence CCTCACTGCCAGATCGCCT (SEQ ID. NO.3).

5. The composition of claim 1, wherein the oligonucleotide primer comprises the sequence TACATCTGCCTGTGTTAC (SEQ ID. NO.4).

6. The composition of claim 1, wherein the oligonucleotide primer comprises the sequence CCTACATCTGCCTGTGTTAC (SEQ ID. NO.5.

7. The composition of claim 1, wherein the oligonucleotide primer comprises the sequence CCGCCATACGTGCTG (SEQ ID. NO.6).

8. The composition of claim 1, wherein the oligonucleotide primer comprises the sequence ATCTGTGGCATACCT (SEQ ID. NO.7).

9. The composition of claim 1, wherein the oligonucleotide primer comprises the sequence GGGAATTCATCTGTGGCATACCT (SEQ ID. NO.8).

10. The composition of claim 1, wherein the oligonucleotide primer comprises a sequence selected from the group consisting of ATCTGTGGCATACCTAAAGG (SEQ ID. NO.9); GAATCGCTTGGCTCG (SEQ ID. NO.10); CCAGATCGCCTTTAAGAAGG (SEQ ID. NO.11); and TACAGGTAGCAGCACGTATG (SEQ ID. NO.12).

11. A method of screening for breast cancer in a human subject comprising a) obtaining a sample of breast cells from a human subject;

b) contacting nucleic acids contained in said sample with the oligonucleotide of claim 1 under conditions wherein said oligonucleotide is capable of specifically hybridizing with a nucleic acid molecule which (I) hybridizes to the env gene of a mouse mammary tumor virus; (ii) is present in at least 38% of DNA samples prepared from breast cancer tissue of different human samples; and (iii) hybridizes to less than 7% of DNA samples prepared from tissues other than breast cancer tissue from different human subjects c) detecting any hybridization products formed, wherein the presence of said hybridization products is positively correlated with an increased susceptibility to breast cancer.

12. The method of claim 11 wherein said oligonucleotide comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO: 9, SEQ ID NO: 10, SEQ ID NO: 11, and SEQ ID NO: 12.

13. The method of claim 11 wherein said contacting is performed in the presence of a polymerase and said hybridization products are amplified prior to said detecting.

14. The method of claim 13 wherein said hybridization products are amplified using polymerase chain reaction (PCR).

* * * * *

UNITED STATES PATENT AND TRADEMARK OFFICE
CERTIFICATE OF CORRECTION

PATENT NO. : 5,686,247  Page 1 of 2
DATED : November 11, 1997
INVENTOR(S) : James Holland, et al.

It is certified that error appears in the above-indentified patent and that said Letters Patent is hereby corrected as shown below:

On the title page:

Item [56], 10<sup>th</sup> line "76: 1087-1097" should read --73-1087-1097--;

Col. 4, line 38, "HERr-K10" should read --HERV-K10--;

Col. 5, line 42, "No. 12" should read --No. 12).--;

Col. 6, line 10, "polyclonal) antibodies" should read --polyclonal antibodies)--;

Col. 7, line 51, "were" should read --where--;

Col. 8, line 61, "envgene" should read --env gene--;

Col. 9, line 4, "envgene" should read -- env gene--;

Col. 10, line 6, "envgene-like" should read --env gene-like--;

Col. 10, line 8, "envgene" should read --env gene--;

Col. 10, line 20, "envgene" should read --env gene--;

Col.10, line 24, "envgene-like: should read --env gene-like--;

UNITED STATES PATENT AND TRADEMARK OFFICE
CERTIFICATE OF CORRECTION

PATENT NO. : 5,686,247
DATED : November 11, 1997
INVENTOR(S) : James Holland, et al.

It is certified that error appears in the above-indentified patent and that said Letters Patent is hereby corrected as shown below:

Col. 10, line 26, "envgene" should read --env gene--;

Col. 12, line 38, "fate" should read --fate of--;

Col. 26, line 40, "samples" should read --subjects--.

Signed and Sealed this

Sixteenth Day of June, 1998

Attest:

BRUCE LEHMAN

*Attesting Officer*    *Commissioner of Patents and Trademarks*